United States Patent
Seleem et al.

(10) Patent No.: US 11,098,014 B2
(45) Date of Patent: *Aug. 24, 2021

(54) ARYL ISONITRILES AS A NEW CLASS OF ANTIMICROBIAL COMPOUNDS

(71) Applicant: Purdue Research Foundation, West Lafayette, IN (US)

(72) Inventors: Mohamed Seleem, West Lafayette, IN (US); Mingji Dai, West Lafayette, IN (US); Dexter Cameron Davis, West Lafayette, IN (US); Haroon Taj Mohammad, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/511,053

(22) Filed: Jul. 15, 2019

(65) Prior Publication Data
US 2019/0352264 A1 Nov. 21, 2019

Related U.S. Application Data

(63) Continuation of application No. 15/090,619, filed on Apr. 4, 2016, now Pat. No. 10,364,224.

(60) Provisional application No. 62/143,031, filed on Apr. 4, 2015.

(51) Int. Cl.
| | |
|---|---|
| *C07D 213/38* | (2006.01) |
| *C07C 291/10* | (2006.01) |
| *A61K 31/277* | (2006.01) |
| *A61K 31/4406* | (2006.01) |
| *A61K 31/4409* | (2006.01) |
| *A61K 31/4402* | (2006.01) |

(52) U.S. Cl.
CPC .......... *C07D 213/38* (2013.01); *A61K 31/277* (2013.01); *C07C 291/10* (2013.01); *A61K 31/4402* (2013.01); *A61K 31/4406* (2013.01); *A61K 31/4409* (2013.01); *C07C 2601/14* (2017.05)

(58) Field of Classification Search
CPC .............. A61K 31/277; A61K 31/4402; A61K 31/4406; A61K 31/4409; C07C 2601/14; C07C 291/10; C07D 213/38
See application file for complete search history.

(56) References Cited

U.S. PATENT DOCUMENTS

| | | | | |
|---|---|---|---|---|
| 10,364,224 | B2* | 7/2019 | Seleem | C07D 213/38 |
| 2007/0292545 | A1 | 12/2007 | Monte et al. | |
| 2019/0330154 | A1* | 10/2019 | Seleem | A61K 31/277 |
| 2019/0352265 | A1* | 11/2019 | Seleem | A61K 31/277 |

FOREIGN PATENT DOCUMENTS

| | | | | |
|---|---|---|---|---|
| WO | WO-9913714 A1 * | 3/1999 | | A61K 31/69 |

OTHER PUBLICATIONS

Zhang et al. Organic Letters, 2014, 16, pp. 1216-1219. (Year: 2014).*
Kabir, et al., New classes of Gram-Positive selective antibacterials: Inhibitors of MRSA and surrogates of the causative agents of anthrax and the tuberculosis, Bioorganic and Medicinal Chemistry Letters, 2008, 18, 5745-5749.
Nitta et al., Antibacterial activity of extracts prepared from tropical or subtropical plants on Methicillin-resistant *Staphylococcus aureus*, Journal of Health Science, 48(3), 273-276.

* cited by examiner

*Primary Examiner* — Kara R McMillian
(74) *Attorney, Agent, or Firm* — Purdue Research Foundation; Zhigang Rao

(57) ABSTRACT

The present invention provides aryl isonitrile compounds that have antibacterial properties. More specifically, the aryl isonitrile compounds of the present invention are potent inhibitors of drug resistant strains of *Staphylococcus aureus*.

8 Claims, 8 Drawing Sheets

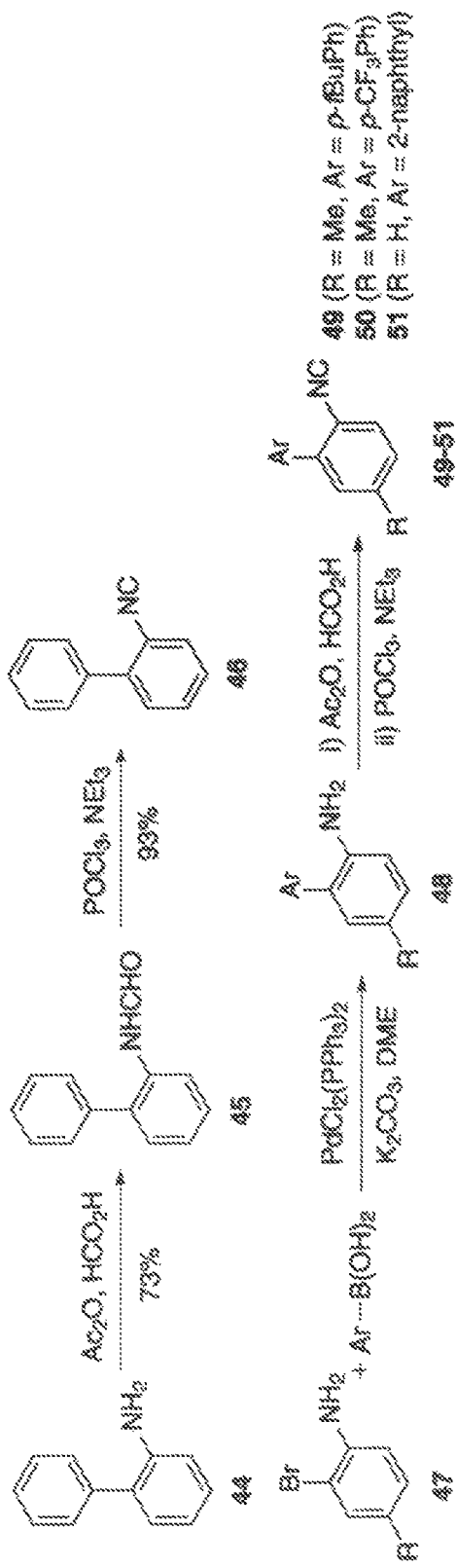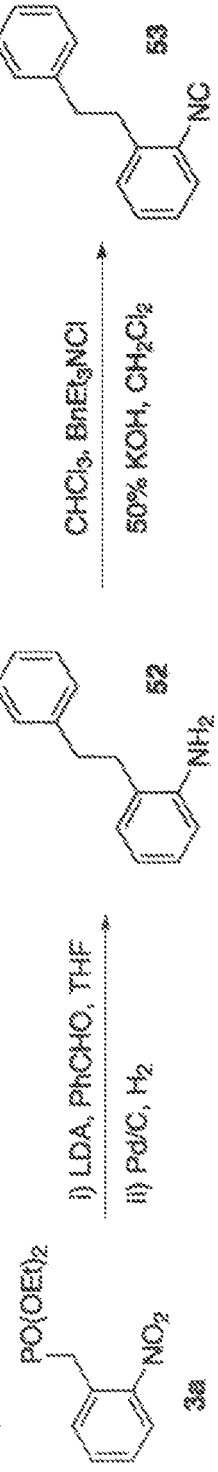
FIGURE 1 (cont'd)

Strains of *Staphylococcus aureus* utilized in this study.

| Strain name | | Isolation | | | Molecular typing | | Antimicrobial resistance phenotype |
|---|---|---|---|---|---|---|---|
| NARSA ID[a] | Alternate designation | Origin | Source | | SCCmec type | spa type | |
| NRS1 | ATCC700699 VISA | Japan | — | | II | TJMBMDMCMK | Resistant to aminoglycosides and tetracycline (minocycline) Glycopeptide-intermediate *S. aureus* |
| NRS72[b] | MSSA 476 | — | — | | — | UKIFKBPE | None |
| NRS119 | SA LinR#12 | United States (Massachusetts) | Dialysis-associated peritonitis | | IV | YHGCMBQBLO | Resistant to linezolid |
| NRS382 | USA100 | United States (Ohio) | Bloodstream | | II | TJMBMDMGMK | Resistant to erythromycin, clindamycin and levofloxacin |
| NRS383 | USA200 | United States (North Carolina) | Bloodstream | | II | WGKAKAOMQQQ | Resistant to erythromycin, clindamycin and gentamicin |
| NRS384 | USA300-0114 | United States (Mississippi) | Wound | | IV | YHGFMBQBLO | Resistant to erythromycin, methicillin, and tetracycline |
| NRS385 | USA500 | United States (Connecticut) | Bloodstream | | IV | YHGCMBQBLO | Resistant to erythromycin, clindamycin, trimethoprim/sulfamethoxazole, levofloxacin, gentamicin and tetracycline |
| NRS386 | USA700 | United States (Louisiana) | Bloodstream | | IV | UJGFMGGM | Resistant to erythromycin and methicillin |
| VRS2 | VRSA | United States (Pennsylvania) | Plantar ulcer | | II | TJMBMDMGMK | Resistant to vancomycin |

[a] NARSA = Network on Antimicrobial Resistance in *Staphylococcus aureus*.
[b] NRS72 = Methicillin-sensitive *Staphylococcus aureus* (MSSA).

FIGURE 2

Minimum inhibitory concentration (MIC, in μM) of isonitrile compounds, linezolid, and vancomycin against methicillin-sensitive (MSSA) and methicillin-resistant *Staphylococcus aureus* (MRSA) strains.

| Compound name | MSSA[a] (NRS72) | MRSA USA100 | MRSA USA200 | MRSA USA300 | MRSA USA500 | MRSA USA700 | MRSA NRS119 | VISA[b] NRS1 | VRSA[c] VRS2 |
|---|---|---|---|---|---|---|---|---|---|
| 1 | 8 | 8 | 16 | 32 | 32 | 8 | 64 | 8 | 32 |
| 4a | >128 | >128 | 128 | >128 | >128 | >128 | >128 | 128 | >128 |
| 5 | 8 | 8 | 64 | >128 | >128 | 16 | >128 | 4 | >128 |
| 6 | 16 | 16 | 16 | 32 | 16 | 16 | 32 | 8 | 32 |
| 7 | 32 | 32 | 32 | >128 | 32 | 16 | >128 | 16 | 64 |
| 8 | 8 | 8 | 8 | 16 | 8 | 4 | 16 | 4 | 16 |
| 9 | 8 | 16 | 16 | 32 | 16 | 8 | 64 | 8 | 32 |
| 10 | 8 | 16 | 16 | 32 | 16 | 16 | 64 | 8 | 16 |
| 11 | 8 | 8 | 8 | 16 | 8 | 4 | >128 | 4 | 8 |
| 12 | 4 | 4 | 8 | >128 | 8 | 2 | 8 | 2 | 8 |
| 13 | 16 | 2 | 4 | 4 | 32 | 4 | 4 | 2 | 32 |
| 14 | 4 | 8 | 2 | 16 | >128 | 8 | 32 | 4 | 32 |
| 15 | 8 | 8 | 4 | 16 | 32 | 16 | 32 | 4 | 32 |
| 16 | 8 | 8 | 8 | 8 | 8 | 8 | 16 | 4 | 16 |
| 17 | 4 | 8 | 2 | 8 | 16 | 8 | 16 | 4 | 32 |
| 18 | 4 | 8 | 2 | 16 | 16 | 8 | 32 | 4 | 32 |
| 19 | 8 | 16 | 16 | 32 | 128 | 16 | 128 | 8 | 128 |
| 20 | 4 | 4 | 2 | 8 | 16 | 2 | 16 | 2 | 16 |
| 21 | 2 | 4 | 4 | 8 | 8 | 4 | 8 | 2 | 8 |
| 22 | 8 | 16 | 16 | 32 | 16 | 16 | >128 | 8 | 32 |
| 23 | 16 | 4 | 4 | 16 | 32 | 8 | 64 | 4 | 32 |
| 24 | >128 | — | >128 | >128 | >128 | — | >128 | — | >128 |
| 25 | 2 | 4 | 4 | 8 | 8 | 8 | 16 | 4 | 8 |
| 26 | 8 | 16 | 64 | >128 | >128 | 16 | >128 | 4 | >128 |
| 27 | 64 | 64 | 64 | 16 | 64 | 32 | 128 | 64 | 32 |
| 28 | 64 | 32 | 64 | 32 | 64 | 64 | 128 | 128 | 128 |
| 29 | 64 | 128 | 128 | 32 | 64 | 128 | 128 | 64 | 64 |
| 30 | 64 | 32 | 32 | 16 | 32 | 32 | 64 | 64 | 32 |
| 31 | 64 | 32 | 64 | 32 | 64 | 64 | 64 | 64 | 64 |
| 32 | 16 | 16 | 32 | 8 | 32 | 16 | 64 | 32 | 8 |
| 33 | 64 | 32 | 32 | 32 | 32 | 32 | 64 | 64 | 64 |
| 34 | 64 | 32 | 64 | 32 | 64 | 64 | 32 | 32 | 64 |
| 35 | 2 | 8 | 8 | 4 | 4 | 8 | 4 | 8 | 4 |
| 36 | 16 | 32 | 32 | 16 | >128 | 16 | 64 | 32 | 32 |
| 37 | 4 | 4 | 32 | 4 | 16 | 64 | >128 | >128 | >128 |
| 42 | >128 | >128 | >128 | >128 | >128 | >128 | >128 | >128 | >128 |
| 43 | >128 | >128 | >128 | >128 | >128 | >128 | >128 | >128 | >128 |
| 46 | >128 | 16 | 16 | >128 | >128 | 16 | >128 | 8 | >128 |
| 49 | >128 | 16 | 16 | >128 | >128 | 16 | 64 | 4 | >128 |
| 50 | >128 | >128 | >128 | >128 | >128 | >128 | >128 | >128 | >128 |
| 51 | 16 | 16 | 64 | 64 | 32 | 16 | 32 | 4 | 64 |
| 52 | >128 | >128 | 32 | >128 | >64 | >64 | >128 | 8 | >64 |
| 53 | 64 | 4 | 16 | 4 | 128 | 32 | 2 | 2 | 64 |
| Linezolid | 2 | <1 | 2 | 2 | <1 | 2 | 64 | <1 | <1 |
| Vancomycin | <1 | 2 | — | — | 4 | — | — | 8 | 128 |

[a] MSSA = Methicillin-sensitive *Staphylococcus aureus*.
[b] VISA = Vancomycin-intermediate *Staphylococcus aureus*.
[c] VRSA = Vancomycin-resistant *Staphylococcus aureus*.

FIGURE 3

| Compound Number | Acceptable Number→ | nViol[1] 1 | cLog P[2] < 5 | MW[3] < 500 | nON[4] < 10 | nOHNH[5] < 5 | tPSA[6] (Å²) |
|---|---|---|---|---|---|---|---|
| 1 | | 0 | 4.635 | 233.31 | 1 | 0 | 4.36 |
| 8 | | 1 | 5.145 | 281.36 | 1 | 0 | 4.36 |
| 11 | | 0 | 4.554 | 263.34 | 2 | 0 | 13.59 |
| 12 | | 1 | 5.318 | 301.31 | 1 | 0 | 4.36 |
| 13 | | 0 | 4.107 | 205.26 | 1 | 0 | 4.36 |
| 14 | | 0 | 4.026 | 235.29 | 2 | 0 | 13.59 |
| 17 | | 0 | 4.25 | 223.25 | 1 | 0 | 4.36 |
| 20 | | 0 | 4.99 | 273.26 | 1 | 0 | 4.36 |
| 23 | | 0 | 4.606 | 219.29 | 1 | 0 | 4.36 |

[1] nViol = number of violations to Lipinski's Rule of 5
[2] cLog P = calculated partition coefficient (Log P)
[3] MW = molecular weight
[4] nON = number of hydrogen bond acceptors
[5] nOHNH = number of hydrogen bond donors
[6] tPSA = topological polar surface area

FIGURE 5

Kinetic solubility assessment of compound 13, reserpine, tamoxifen, and verapamil in phosphate-buffered saline (PBS).

| Compound tested | Solubility limit (μM)[a] | Solubility analysis |
| --- | --- | --- |
| 13 | 15.6 | Low solubility |
| Reserpine | 15.6 | Low solubility |
| Tamoxifen | 15.6 | Low solubility |
| Verapamil | >500 | High solubility |

[a] Solubility limit corresponds to the highest concentration of test compound where no precipitate was detected.

FIGURE 6

Permeability analysis of compound 13, ranitidine, warfarin, and talinolol via the Caco-2 permeability assay.

| Compound/drug tested | Mean A → B $P_{app}$ ($10^{-6}$ cm/s) | Mean B → A $P_{app}$ ($10^{-6}$ cm/s) | Efflux ratio[c] | Permeability analysis |
|---|---|---|---|---|
| 13 | 0.0[d] | 0.0 | N/A[e] | Not permeable |
| Ranitidine | 0.23 | 3.1 | 13.5 | Low permeability |
| Warfarin | 27.0 | 7.2 | 0.3 | High permeability |
| Talinolol | 0.05 | 8.9 | 178 | P-gp[f] efflux control |

[a] Mean A → B $P_{app}$ = mean apparent permeability of test compound from apical to basolateral surface.
[b] Mean B → A $P_{app}$ = mean apparent permeability of test compound from basolateral to apical surface.
[c] Efflux ratio = $P_{app}(B \to A)/P_{app}(A \to B)$.
[d] Compound not detected in receiver compartment.
[e] N/A, not applicable.
[f] P-gp, P-glycoprotein.

FIGURE 7

Evaluation of metabolic stability of compound 13, verapamil, and warfarin in human liver microsomes.

| Compound/drug tested | Average remaining after 60 min (%), with NADPH | Average remaining after 60 min (%), without NADPH | Notes |
|---|---|---|---|
| 13 | 24 | 51 | — |
| Verapamil | 13 | 94 | High metabolism control |
| Warfarin | 93 | 94 | Low metabolism control |

FIGURE 8

ARYL ISONITRILES AS A NEW CLASS OF ANTIMICROBIAL COMPOUNDS

BACKGROUND OF THE INVENTION

This invention is directed generally to new antimicrobial compounds and more specifically, to aryl isonitrile compounds as a new class of antimicrobial compounds.

Multidrug-resistant bacterial infections pose a significant global health challenge afflicting more than 2 million people each year in the United States alone, resulting in over 23,000 fatalities. Nearly half of these casualties are due to infections caused by a single pathogen, methicillin-resistant *Staphylococcus aureus* (MRSA). Currently prevalent in the community setting, MRSA is responsible for a wide spectrum of illnesses from superficial skin infections to invasive diseases including pneumonia, osteomyelitis, and bloodstream infections. While a robust arsenal of antibiotics was once capable of treating MRSA infections, strains of this pathogen have emerged that exhibit resistance to nearly every class of antibiotics, including agents of last resort such as vancomycin and linezolid.

As can be seen, there is a need for need for the identification and development of novel therapeutic options capable of treating infections due to MRSA.

SUMMARY OF THE INVENTION

In one aspect of the present invention there is provided an aryl isonitrile compound having the general structure of compound I

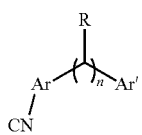

(I)

wherein the compound comprises two aryl moieties linked preferably by an alkyl chain, wherein n may be an integer from 1 to about 3. Alternatively, when n=0, the aryl moieties may be directly linked to one another. It has been shown that the critical component for antimicrobial activity is the isonitrile substituent on one of the aryl moieties (Ar). The position of the aryl isonitrile group is not critical and may be anywhere on the aryl moiety. In another aspect of the present invention, Ar and Ar' may be the same aryl moiety or they may be different. Ar and Ar' may be a five-membered, six-membered or seven-membered ring, or may even be larger. Furthermore, Ar' may be a heteroaryl ring, comprising an oxygen or nitrogen in place of a ring carbon. Ar' may also comprise a substituent. The substituent may be a C1 to C3 alkyl group, a halogen, alkyloxy, trihalomethyl, or a nitro group.

These and other features, aspects and advantages of the present invention will become better understood with reference to the following drawings, description and claims.

BRIEF DESCRIPTION OF THE DRAWINGS

FIG. 2 is a table listing the strains of *Staphylococcus aureus* utilized to test the antimicrobial properties of exemplary compounds of the present invention;

FIG. 3 is a table showing the minimum inhibitory concentration (MIC) of isonitrile compounds, linezolid, and vancomycin against methicillin-sensitive (MSSA) and methicillin-resistant *S. aureus* (MRSA) strains;

FIG. 5 is a table listing the calculation of physicochemical properties of exemplary compounds of the present invention for Lipinski's Rule of 5;

FIG. 6 is a table of kinetic solubility assessment of compound 13 of the present invention, reserpine, tamoxifen and verapamil in PBS;

FIG. 7 is a table of permeability analysis of compound 13 of the present invention, ranitidine, warfarin and talinolol via the Caco-2 permeability assay; and FIG. 8 is a table of the evaluation of metabolic stability of exemplary compound 13, verapamil and warfarin in human liver microsomes.

DETAILED DESCRIPTION OF THE INVENTION

Figure 1:
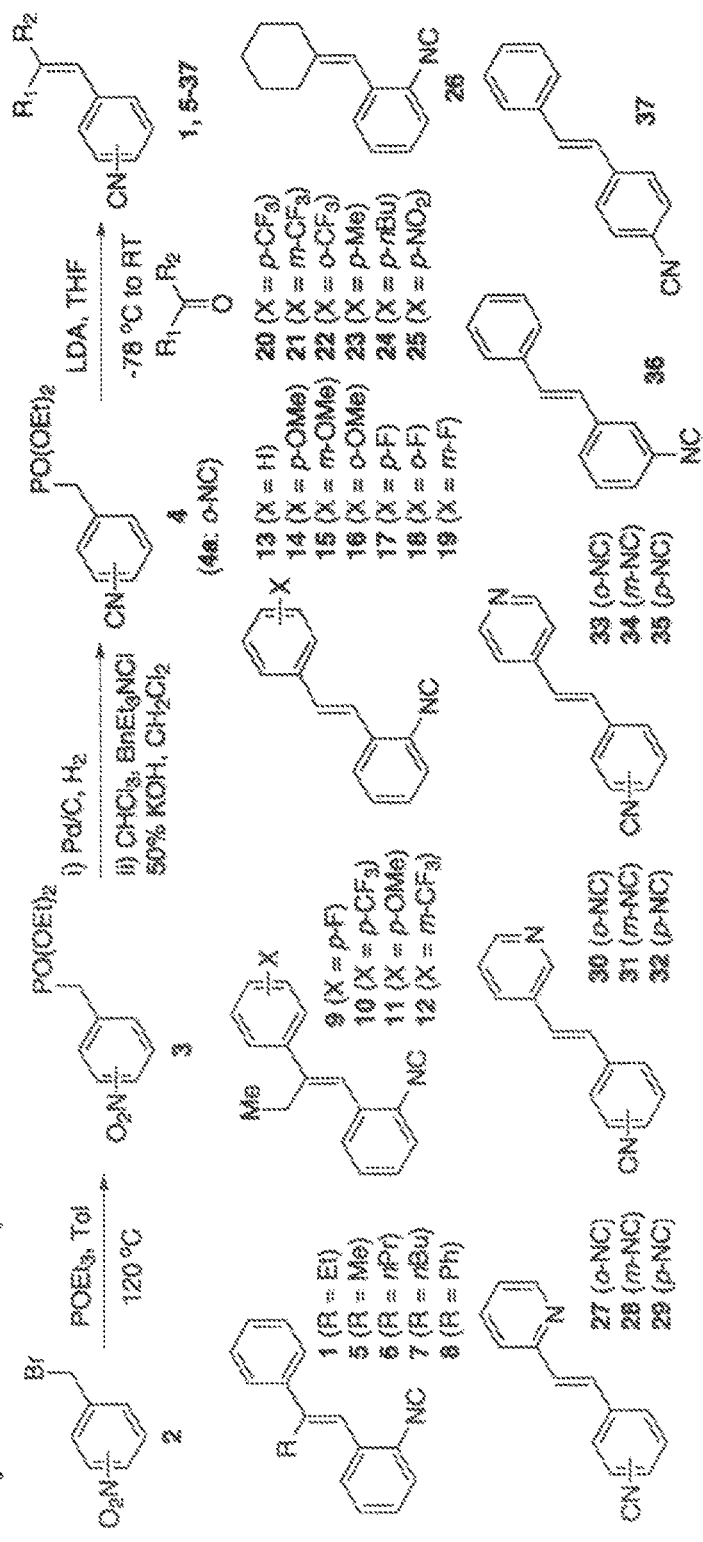
FIG. 1 is a scheme showing the structure and synthesis of exemplary compounds of one aspect of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides novel aryl isonitrile compounds, wherein the compounds comprise two aryl moieties linked by an alkyl chain and wherein one of the aryl groups comprises an isonitrile substituent. Methods of use are also provided for the treatment of drug resistant bacteria, in particular, drug-sensitive and drug-resistant *Staphylococcus aureus*, commonly referred to as MRSA or MSSA. For the ease of description, MRSA will be used to refer to all strains of drug-sensitive and drug resistant *S. aureus*.

The compounds of the present invention are able to inhibit bacterial growth at micromolar concentrations while showing no toxicity to mammalian cells. This is in contrast to the state of the art, wherein there is a lack of new antibiotic compounds to treat MRSA infections.

In one aspect of the present invention there is provided an aryl isonitrile compound having the general structure of compound I

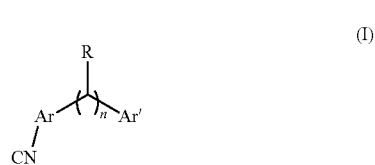

(I)

wherein the compound comprises two aryl moieties linked preferably by an alkyl chain, wherein n may be an integer from 1 to about 3. Alternatively, when n=0, the aryl moieties may be directly linked to one another. It has been shown that the critical component for antimicrobial activity is the isonitrile substituent on one of the aryl moieties (Ar). The position of the aryl isonitrile group is not critical and may be anywhere on the aryl moiety. In another aspect of the present invention, Ar and Ar' may be the same aryl moiety or they may be different. Ar and Ar' may be a five-membered, six-membered or seven-membered ring, or may even be larger. Furthermore, Ar' may be a heteroaryl ring, comprising an oxygen or nitrogen in place of a ring carbon. Ar' may also comprise a substituent. The substituent may be a C1 to C3 alkyl group, a halogen, alkyloxy, trihalomethyl, or a nitro group.

In another aspect of the present invention, the alkyl chain may be an alkane or an alkene. Preferably the alkyl chain, or bridge, between the two aryl moieties is an alkene. It has been shown (see Example) that compounds comprising an alkane bridge have a significantly lower antibiotic activity against MRSA than compound with an alkene bridge between the two aryl moieties, Ar and Ar'. However, the compounds with an alkane bridge did have antibiotic activity against several MRSA strains.

In a further aspect of the present invention, the alkyl bridge may comprise a substituent. The substituent may be hydrogen, a C1 to C3 alkyl group, a halogen, alkyloxy, trihalomethyl, or a nitro group.

In another aspect of the present invention, there is provided an aryl isonitrile compound having the structure of compound II or III:

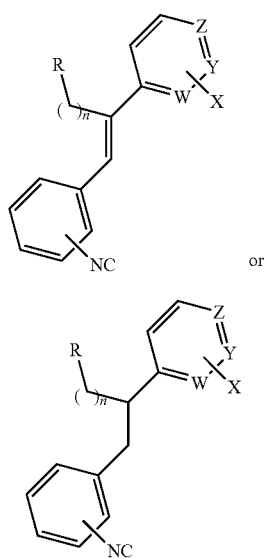

wherein R is an alkyl, a cycloalkyl, a heteroalkyl, or an aryl group;
n is an integer from 0 to 4;
X is hydrogen, a C1 to C3 alkyl group, a halogen, alkyloxy, trihalomethyl, or a nitro group;
W, Y and Z are each independently —CH—, —N— or —O—; and
pharmaceutically acceptable salts thereof.

Exemplary compounds of the present invention having structures II or III are given in FIG. 1. In an exemplary embodiment, R is a methyl group and n is an integer from 0 to 4. Alternatively, compounds II and III may lack substituent R on the alkyl bridge. In another aspect of the present invention, X may be a hydrogen, a C1-C3 alkyl group (i.e. methyl, ethyl, n-propyl or n-butyl), a halogen, such as, but not limited to fluorine (F), an alkoxy such as, but not limited to methoxy, a trihalomethyl such as but not limited to trifluoromethyl or a nitro group.

In another aspect of the present invention, methods are providing for inhibiting MRSA by treating the MRSA with the compounds of the present invention. Exemplary strains of MRSA that may be inhibited by the compounds of the present invention are provided in FIGS. 2 and 3. The methods may comprise the steps of contacting the MRSA with an inhibitory amount of the compounds of the present invention. In one aspect of the present invention, the compounds may be from about 50 µM to about 100 µM.

Alternatively, methods are provided for treating a patient with MRSA comprising administering a therapeutic amount of the compounds of the present invention to a patient having MRSA. It will be appreciated that the amount of compound to be administered with depend on the strain of MRSA and the severity of the infection. The amount may be determined by the skilled practitioner without undue experimentation. The compounds may be administered in a manner consistent with treatment of a MRSA infection. In one exemplary aspect, the compounds are administered systemically in a pharmaceutically acceptable carrier. In another exemplary aspect of the present invention, the compounds may be administered topically. This would be desirable if the MRSA infection is a skin infection. Moreover, the compounds of the present invention may be administered along with other compounds to treat the MRSA infection.

EXAMPLE

A whole-cell screening of a small number of in house generated small molecules with diverse structural skeletons (about 250 molecules) has been conducted against MRSA USA300 with the aim to identify compounds with novel skeletons to target antibiotic drug resistance. Among several hit molecules revealed by this mini-screening effort, compound I with an isonitrile group attached to a stilbene system was shown to be capable of inhibiting bacterial growth at a concentration of 32 µM (FIG. 1). The presence of an isonitrile moiety in this compound is quite unique given that few antimicrobial compounds possessing the isonitrile moiety in their core structure have been described in literature and those that have been are natural products. Marconi, G. G. et al., J. Antibiot. 1978, 31, 27-32; Mo, S. et al., J. Nat. Prod. 2009, 72, 894-899; Raveh, A. et al., J. Nat. Prod. 2007, 70, 196-201; Sugawara, T. et al., J. Antibiot. 1997, 50, 944-948; Fujiwara, A. et al., Agric. Biol. Chem. 1982, 46, 1803-1809. Marquez, J. A. et al., J. Antibiot. 1983, 36, 1101-1108. The novel structural skeleton of compound I as an antibacterial compound against drug resistant strains prompted further study of these types of isonitrile compounds. Herein is reported the chemical synthesis, structure-activity relationship study, and evaluation of the antibacterial performance of compound 1 and closely related analogs against several clinically-relevant MRSA and VRSA strains. These efforts have led to the identification of more potent compounds with MIC as low as 2 µM but do not show any cytotoxicity against mammalian cells up to a concentration of 64 µM. Physiochemical analysis of several potent lead compounds has been described to guide the next stage of developing these promising compounds into the antibiotic drug pipeline.

Chemistry:

In general, the stilbene isonitrile analogs were prepared from benzylic bromide 2 (FIG. 1) which was converted to phosphonate 3 by Michaelis-Arbuzov reaction. (Abruzov, B. A. et al., Pure. Appl. Chem. 9 (1964) 307-353. The nitro group of 3 was then converted to an isonitrile group upon a sequence of hydrogenation and Hofmann isonitrile synthesis using dichlorocarbene. Weber W. P. & Gokel G. W., Tetrahedron Lett. (1972) 1637-1640. Compound 4 then served as a divergent point to synthesize a collection of analogs with a Horner-Wadsworth-Emmons reaction. Zhang, B. & Studer, A., *Org. Lett.* 2014, 16, 1216-1219. By treating various ketones and aldehydes with stabilized phosphonate carbanions derived from phosphonates 4, thirty-three stilbene isonitrile analogs (1, 5-25 and 27-37) and one styrene isonitrile analog (26) were obtained. This collection also included compounds with the isonitrile group at different positions on the aromatic ring as well as pyridine containing analogs. In order to investigate the importance of the isonitrile group for the observed biological activity, compounds containing a hydrogen atom (42) or a nitrile group (43) at the isonitrile-substitution position were prepared as well using the Horner-Wadsworth-Emmons reaction. Additionally, four biaryl isonitrile analogs (46 and 49-51) were prepared. Zhang, B. et al., *Angew. Chem. Int. Ed.* 2013, 52, 10792-10795. Compound 46 was prepared from commercially available amine 44 via form-amide formation followed by dehydration. Compounds 49-51 were synthesized from 2-bromoaniline derivatives (47) and aryl-boronic acids. Suzuki cross-coupling converted 47 to biaryl amines 48 smoothly. The latter was then converted to 49-51 via the aforementioned formamide formation and dehydration sequence. Lastly, compound 53 was prepared with a saturated two-carbon chain to investigate the importance of the double bond linker between the two aromatic moieties. All the newly synthesized compounds were purified using flash chromatography before entering biological evaluations.

Biological Results and Discussion:

Antimicrobial Susceptibility Analysis of the Isonitrile Compounds Against Clinically Relevant Isolates of MRSA.

The bacterial growth inhibiting activity of these synthetic analogs of hit compound 1 were subsequently evaluated (FIG. 3). When these derivatives were screened against MRSA via the broth microdilution assay, the results revealed several interesting structural elements that appeared to play an important role in the antimicrobial activity of these compounds. Initial inspection of the structural moieties of 1 revealed that the presence of an isonitrile group was essential for its antimicrobial activity. When the isonitrile group of 1 (MIC against MRSA ranging from 8-64 µM) was removed (as in compound 42), a complete loss in the anti-MRSA activity of 42 was observed (MIC>128 µM). A similar pattern was observed when reviewing the MIC results for compounds 13 and 43. Compound 13, one of the most potent derivatives constructed (with MIC values against MRSA as low as 2 µM), contains the isonitrile group; when the isonitrile group of 13 is replaced with an isosteric nitrile group (resulting in compound 43), complete loss of antimicrobial activity was observed. Similarly, compound 53 with an isonitrile group is active against several strains evaluated particularly MRSA USA100, MRSA USA300, MRSA NRS119, and VISA NRS1, while compound 52 without the isonitrile group lacks antimicrobial activity. These results confirm that the isonitrile group appears necessary for these compounds to possess activity against MRSA and may play an important role in binding to the compound's molecular target.

The presence of a second aromatic substituent (connected to the isonitrile-phenyl group) also appeared critical to the biological activity observed; replacement of this moiety in 1 with a diethyl phosphonate (as in analogue 4a with an ortho-isonitrile group) resulted in complete loss of activity against MRSA (MIC>128 µM). Likewise, substitution of this second aromatic substituent with a cycloalkane (cf. 26) rendered this compound inactive against several MRSA isolates (including MRSA USA300, MRSA USA500, and MRSA NRS119). The presence of an alkene bridge between the two aromatic substituents in 1 also appeared to be important. When the alkene bridge between the two aromatic substituents was removed, as in compound 46, the compound lacked activity against three strains of MRSA (USA300, USA500, and NRS119). A similar loss in antimicrobial activity was observed with compounds 49 and 50 indicating that the stilbene isonitrile core of 1 plays an important role in its antimicrobial activity. This notion was further supported by a direct comparison of compounds 13 and 53. Compound 53 is a saturated analog of compound 13 and contains a flexible two-carbon linker between the two aromatic moieties. In general, compound 53 is less potent than compound 13 against all the strains texted except for VISA NRS1.

It was then evaluated how substituents on the double bond would affect the antimicrobial activity. Interestingly, removal of the ethyl group of 1 (cf. 13) resulted in a dramatic improvement in antimicrobial activity (a two-to-eight fold reduction in the MIC against MRSA was observed). When the ethyl group was replaced by methyl (5), n-propyl (6), n-butyl (7) and phenyl (8) groups, a noticeable change in the MIC value for these compounds was observed.

It was next assessed how substituents on the non-isonitrile-containing aromatic ring would affect the potency against MRSA. Analogues constructed included substitution of methoxy group (14-16), fluoride (17-19), trifluoromethyl group (20-22), methyl group (23), n-butyl group (24), and nitro group (25). Interestingly most of these modifications did not produce a major improvement in the MIC observed against MRSA, when compared to the activity of 13. Additionally the positioning of these groups around the benzene ring did not appear to have an impact on the antimicrobial activity of the compound. While most of these modifications had little effect on improving the antimicrobial activity of these compounds, one substitution had an observed deleterious effect. Compound 24, containing a n-butyl group, lacked activity against most MRSA strains tested (MIC>128 µM); interestingly, 23, with a methyl group was active against all MRSA strains tested albeit at a higher concentration than 13 (MIC of 23 ranges from 4 to 64 µM against MRSA). This would appear to indicate that the presence of an alkyl group (in particular one of increased length) is undesirable and can have a negative effect on the activity of these compounds against MRSA. Analogs containing a pyridine ring were synthesized and tested as well (27, 30, and 33) and reduced antimicrobial activities were observed.

All the analogs discussed above contain an ortho-substituted isonitrile group. It was wondered how the relative position of the isonitrile group would affect the antimicrobial activity and prepared eight analogs with the isonitrile group in para- and meta-relationship to the double bond (cf. 28, 29, 31, 32, 34-37). Different antimicrobial activity patterns are observed. For the group of 13, 36, and 37, the ortho-substituted compound 13 is still the most potent one against most of the strains tested and slight improvement was observed for the para-substituted compound 37 against MSSA (NRS72) and MRSA USA500. Interestingly, for the group of 33, 34, and 35, the para-substituted compound 35 is much more active against all the strains tested than the ortho- and meta-substituted ones. The groups of 27-29 and 30-32 are less potent than the aforementioned two groups, which indicate that the position of the nitrogen atom in the pyridine ring is important for the observed antimicrobial activity as well.

After completing a preliminary examination of the structure-activity relationship of these compounds, it was assessed whether these compounds would retain their activity against several of the most challenging strains of MRSA (FIGS. 2 and 3). When tested against an array of clinically relevant MRSA isolates, the most potent compounds (6, 8-18, 20-21, 25 and 37) did retain their antimicrobial activity. Indeed these compounds possessed potent activity against MRSA isolates prevalent in the healthcare setting such as MRSA USA100 (responsible for invasive diseases in infected hospitalized patients), and MRSA USA200 (associated with more severe morbidity in affected patients due to the production of toxins that can lead to toxic shock syndrome). In addition to this, these compounds exhibited potent activity against MRSA USA300, a strain that has been linked to the majority of MRSA skin and soft tissue infections present in the community setting. Furthermore, these compounds demonstrated strong antimicrobial activity against MRSA strains exhibiting resistance to numerous antibiotic classes including penicillins, aminoglycosides (NRS1, USA200, and USA500), macrolides (USA100, USA200, USA300, USA500, and USA700), lincosamides (USA100, USA200, USA500), tetracyclines (NRS1, USA300, and USA500), and fluoroquinolones (USA100 and USA500). Additionally, compounds 10, 11, 12, 21, 25, 32 and 35 exhibited potent antimicrobial activity (MIC between 2 and 16 µM) against clinical isolates of S. aureus exhibiting resistance to antibiotics deemed agents of last resort, namely vancomycin (VRS2). These results indicated cross-resistance between these antibiotics and the aryl isonitrile compounds is unlikely; this lends further credence to the notion that the aryl isonitrile compounds may have potential to be developed as future alternatives to these antibiotics.

Toxicity Analysis of Most Potent Aryl Isonitrile Compounds Against Mammalian Cells.

Figure 4:
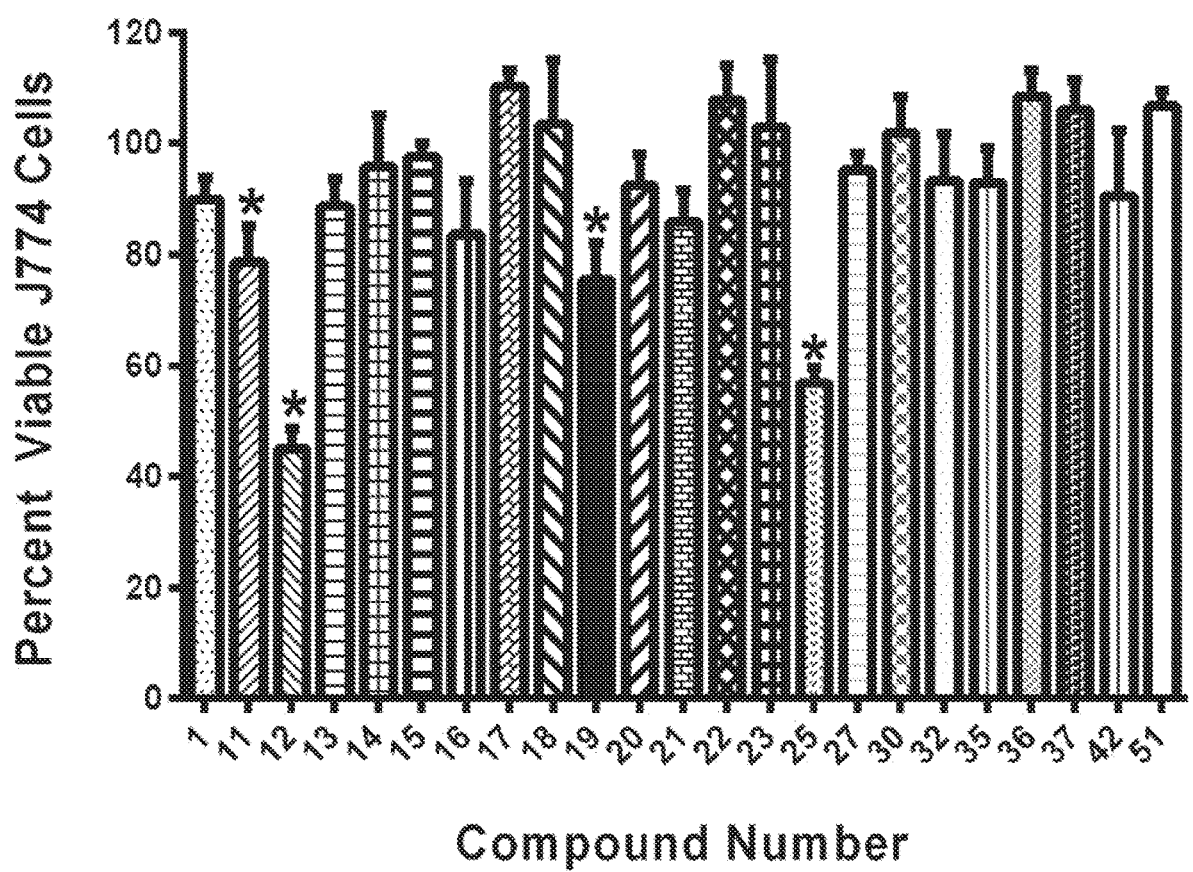
FIG. 4 is a bar graph showing the cytotoxicity analysis of exemplary compounds of the present with mammalian cells.

Identification of compounds exhibiting potent antimicrobial activity is the first step in a lengthy process for drug development. However, many compounds with promising antimicrobial activity fail to advance further in this process due to concerns about toxicity to mammalian tissues. Selective toxicity is a critical feature novel antimicrobial compounds must possess. The ability for antimicrobial agents to exhibit their activity on the target microorganism while not causing harm to host (mammalian) tissues is important to ascertain early in the drug discovery process. To determine if compound 1 and fifteen of its most potent derivatives against MRSA exhibited toxicity to mammalian tissues, these compounds were screened against a murine macrophage (J774) cell line utilizing the MTS assay (FIG. 4). Initial inspection of the structure-activity relationship revealed that the isonitrile moiety appeared to be a vital component in the antimicrobial activity of these compounds. This was a point of concern given the isonitrile group has been associated with a high degree of toxicity in certain compounds present in nature. Goda, M. et al., *J. Biol. Chem.* 2001, 276, 23480-23485. However, when the most potent compound, 13 (containing the isonitrile moiety), and its analogue 42 (lacking the isonitrile moiety) were tested against J774 cells, they produced identical results (neither compound was toxic up to a concentration of 64 µM). This would indicate that the isonitrile group in these compounds does not contribute to undesirable toxicity to mammalian cells. This result is similar to a study conducted at Bayer AG that found compounds, in their discovery pipeline, containing the isonitrile moiety were not toxic to mice when administered orally or subcutaneously (even at concentrations in excess of 500 mg/kg). Ugi, I. et al., *Angew. Chem. Int. Ed.* 1965, 4, 472-484. In addition to this, at a concentration of 32 µM, all of the compounds tested, with the exception of 25 with a nitro group, were not toxic. When the compounds were tested at a concentration of 64 µM, thirteen out of seventeen compounds were found to not be toxic to J774 cells. Compounds 11, 12, 19, and 25 were found to be toxic at 64 µM. When the compounds were tested at 128 µM, all compounds were found to be toxic with the exception of compounds 15, 30 and 37. For the most active compounds (such as 13), a 16-to-32-fold difference exists between the concentrations at which the compounds exhibit anti-MRSA activity (MIC) compared to the concentration where toxicity is observed.

Preliminary Study of Physicochemical Properties of the Isonitrile Compounds Using Lipinski's Rule of 5, Kinetic Solubility Analysis, and Caco-2 Permeability Assay.

After confirming twelve isonitrile compounds exhibited strong antimicrobial activity against MRSA and were not toxic to mammalian cells up to a concentration of 64 µM, the physicochemical properties of nine representative compounds was analyzed. These properties play an important role in determining the appropriate route of administration (i.e. systemic vs. local) by which compounds with biological activity can be delivered to the host. Kerns, E. H. & Di, L. *Drug-like properties: concepts, structure design and methods-from ADME to toxicity optimization.* Amsterdam; Boston: Academic Press; 2008. Additionally, the physicochemical properties of a compound will have a direct impact on its pharmacokinetic profile (in particular absorption and metabolism), providing important information on the likelihood of attaining success in translating a promising compound into a viable drug candidate. Compounds possessing a limited physicochemical profile can have issues pertaining to solubility (limiting the ability of a drug to be absorbed from the intestinal tract) and permeability which can hinder a compound's ability to cross biological membranes, reach the bloodstream, and arrive at the target site of an infection (thus limiting their use systemically). Analysis of the hydrogen bonding potential and lipophilicity of promising compounds can lend valuable insight into probable issues pertaining to solubility and permeability. Utilizing Lipinski's Rule of 5 (Lipinski, C. A. et al., *Adv. Drug Deliv. Rev.* 2001, 46, 3-26) and topological polar surface area (tPSA) as guidelines, it was predicted whether the most promising isonitrile compounds disclosed herein would have suitable physicochemical properties to allow them to be used in systemic applications. Compounds violating more than one principle in the Rule of 5 would be expected to have issues pertaining to solubility and permeability.

As depicted in the table of FIG. 5, seven out of nine compounds analyzed (including the most promising compound 13) possessed calculated log P (clog P) and tPSA values that would indicate that these compounds should not experience issues pertaining to both solubility and permeability. Two derivatives (8 and 12) possessed a clog P value above five, which is a violation to the Rule of 5. This particular violation would suggest difficulty in the ability of these compounds to passively cross a biological membrane. No significant difference is observed in the number of hydrogen bond donor (zero) and acceptor (1-2) groups present in the structure of the compounds analyzed, which would indicate that they would be expected to share a similar solubility profile. As compound 13 was the most promising compound identified thus far (with MIC values as low as 2 µM against MRSA, exhibiting no toxicity to mammalian cells up to a concentration of 64 µM, and possessing zero violations to the Rule of 5), this analogue was selected for further analysis.

To confirm if the prediction of 13 having a good physicochemical profile was accurate, a kinetic solubility screen (using phosphate-buffered saline) and Caco-2 permeability analysis was performed with this compound. The solubility screen determined the highest concentration 13 and three control drugs were capable of being fully dissolved in an aqueous solvent (PBS). As presented in the table of FIG. 6, this experiment revealed that compound 13 possessed partial aqueous solubility (soluble up to 15.6 µM), identical to the control drugs reserpine and tamoxifen.

The Caco-2 permeability assay revealed that compound 13 was not able to permeate across the Caco-2 bilayer. As presented in the table in FIG. 7, this compound was unable to cross from the apical (A) to basolateral (B) surface of the membrane (apparent permeability, Papp=0.0 cm/sec). A similar pattern was observed in the basolateral to apical direction with Papp=0.0 cm/sec (indicating this compound is unlikely a substrate for an efflux transporter, like talinolol, which would be one plausible explanation for the inability of this compound to traverse the membrane). This is in stark contrast to the control drug warfarin, which is able to effectively permeate across the membrane from the basolateral to apical surface (Papp=27.0×10-6 cm/sec). This result is a bit surprising given the size, structure, and calculated partition coefficient (clog P=4.107) for 13. Thus, in addition to possessing only partial aqueous solubility, 13 also possesses a poor permeability profile, indicating that, in its present state, this compound would not be suitable for use systemically.

The result from the Caco-2 permeability analysis is in agreement with the overall result obtained from the kinetic solubility screen indicating that 13, though a promising antimicrobial candidate, needs to undergo further structural modifications to enhance its physicochemical profile in order for it to be used systemically. In addition to modifying the structure of this compound, formulation technology can be utilized to overcome this compound's current limitations. This technology has been used to improve the drug-like properties of promising compounds with similar kinetic profiles to 13 in order to propel these compounds into further stages of drug development. By using a spray drying dispersion technique (Kwong, A. D. et al., *Nat. Biotechnol.* 2011, 29, 993-1003), the antisolvent crystallization method (Lonare, A. A. & Patel, S. R., *Int. J. Chem. Eng. Appl.* 2013, 4, 337-341), or combining the active compound with an excipient to create an amorphous solid dispersion (Van den Mooter, G., *Drug Discov. Today. Technol.* 2012, 9, e71-e174), the aqueous solubility, permeability and bioavailability profile of this compound may be significantly improved. Identifying that 13 has a problematic physicochemical profile early in the drug discovery process will permit medicinal chemists and formulation scientists to invest time and effort to enhancing both the physiochemical and pharmacokinetic profiles of this promising new antimicrobial compound.

Metabolic Stability Analysis of 13 Via Microsomal Stability Analysis.

In addition to studying the solubility and permeability profile of compound 13, the stability of this compound to metabolic processes present in the liver was investigated using human liver microsomes (FIG. 8). Drugs administered systemically often are subject to various metabolic processes that can convert the active compound to inactive metabolites. Pharmaceutical compounds that are slow to be metabolized have multiple advantages including an improved pharmacokinetic profile, reduced frequency of doses that need to be given to patients (leading to better patient compliance), while also ensuring the active drug circulates within the patient's system to assist with treating and clearing an infection. As the liver is the primary organ for metabolism of drugs administered systemically in the body, incubating compounds with liver microsomes can shed valuable insight into the stability of these compounds to metabolic processes.

When 13 was incubated with human liver microsomes, it was found to be rapidly metabolized (only 24% of the parent compound remained after one hour) similar to the highly metabolized control drug, verapamil (13% remained after one hour incubation with liver microsomes) (FIG. 11). While verapamil appeared to be metabolized via a NADPH-mediated process (as 94% of the drug remained after one hour when the co-factor NADPH was removed from the reaction mixture), 13 does not appear to mimic this result as only 51% of the parent compound remained after one hour when NADPH was not present. This would appear to suggest that 13 is metabolized by more than one enzyme system/reaction (one dependent on the co-factor NADPH (most likely the cytochrome P450 system), and one independent of NADPH). The metabolic stability analysis performed lends further credence to the argument that in their present state, 13, would not be suitable for use in systemic applications to treat MRSA infections.

Methods: Synthetic Procedures and Spectra Data

General Methods.

Reactions were performed using standard syringe techniques under argon unless stated otherwise. Starting materials and reagents were used as received from suppliers (Aldrich, Alfa Aeser, Acros). Anhydrous THF was distilled over sodium benzophenone under argon. Acetonitrile (CH3CN), dichloromethane (CH2Cl2), methanol (MeOH), and toluene were purified by passing the previously degassed solvents through activated alumina columns. Flash chromatography was performed using silica gel (230-400 mesh). Thin layer chromatography (TLC) was performed using glass-backed silica plates (Silicycle). NMR spectra were recorded on a Bruker ARX-300, Bruker ARX-400 spectrometer, DRX-500 or AV-500 spectrometer at room temperature. Chemical shifts (in ppm) are given in reference to the solvent signal [1H NMR: CDCl3 (7.26); 13C NMR: CDCl3 (77.2).]. 1H NMR data are reported as follows: chemical shifts ($\delta$ ppm), multiplicity (s=singlet, d=doublet, t=triplet, q=quartet, m=multiplet, br=broad), coupling constant (Hz), and integration. 13C NMR data are reported in terms of chemical shift and multiplicity. IR data were recorded on a Thermo Nicolet Nexus 470 FTIR.

A Representative Procedure for the Synthesis of Aryl Isonitriles:

(E)-1-isocyano-2-(2-phenylbut-1-en-1-yl)benzene (1)

To a stirred solution of diisopropyl amine (52 mg, 0.52 mmol) in THF (1.3 ml) was added a solution of n-BuLi (2.5 M in hexane, 0.174 ml, 0.43 mmol) dropwise at −78° C. After stirring for 5 min, a solution of diethyl (2-isocyanobenzyl)phosphonate 4 (100 mg, 0.395 mmol) in THF (1 ml) was added dropwise at −78° C. The resulting solution was stirred for an additional 30 min and a solution of propiophenone (48 mg, 0.36 mmol) in THF (1 ml) was added dropwise. The reaction was stirred for an additional 30 min at −78° C. then warmed to room temperature and stirred for 1 h. A saturated aqueous ammonium chloride solution (4 ml) and Et2O (4 ml) were added. The aqueous layer was extracted with Et2O (3×5 ml) and the combined organic layers were washed with brine (10 ml), dried over anhydrous sodium sulfate and concentrated under reduced pressure.

The resulting residue was purified by flash chromatography (CH2Cl2/hexane=1/4) to yield (E)-1-isocyano-2-(2-phenyl-but-1-en-1-yl)benzene 1 (50 mg, 60% yield.)

$^1$H NMR (300 MHz, CDCl3) δ 7.35-7.17 (m, 4H), 7.20-6.99 (m, 3H), 6.96 (td, J=7.7, 1.4 Hz, 1H), 6.78 (dd, J=7.9, 1.5 Hz, 1H), 6.63 (s, 1H), 2.62 (qd, J=7.4, 1.5 Hz, 2H), 1.14 (t, J=7.4 Hz, 3H); $^{13}$C NMR (100 MHz, CDCl3) δ 166.1, 149.1, 140.3, 134.7, 130.2, 128.3 (3C), 128.2, 127.2, 126.7, 126.5, 119.7, 33.0, 12.8.

Spectra Data of New Aryl Isonitriles:

(E)-1-isocyano-2-(2-phenylhex-1-en-1-yl)benzene (7)

$^1$H NMR (500 MHz, CDCl3) δ 7.66-7.19 (m, 4H), 7.19-7.04 (m, 3H), 6.95 (td, J=7.7, 1.3 Hz, 1H), 6.75 (d, J=10 Hz, 1H), 6.60 (s, 1H), 2.59 (t, J=7.5 Hz, 2H), 1.32-1.56 (m, 4H), 0.91 (t, J=7 Hz, 3H); $^{13}$C NMR (125 MHz, CDCl3) δ 165.9, 147.8, 140.3, 134.9, 130.3, 128.5 (2C), 128.4, 128.3, 127.3, 126.8, 126.6, 120.8, 39.8, 30.0, 22.2, 13.9; IR (neat): 2956, 2925, 2854, 2117, 1478, 1448 cm$^{-1}$; MS (ESI): m/z=284.14 calc. for C19H19N[M+Na]+, found 284.24.

(2-(2-isocyanophenyl)ethene-1,1-diyl)dibenzene (8)

$^1$H NMR (500 MHz, CDCl3) δ 7.38-7.28 (m, 8H), 7.16-7.11 (m, 3H), 7.10 (s, 1H), 7.00 (dt, J=8.2, 1.1 Hz, 1H), 6.85 (d, J=8.0 Hz, 1H); $^{13}$C NMR (125 MHz, CDCl3) δ 166.5, 146.7, 142.4, 139.5, 134.6, 130.4, 130.2, 128.5, 128.4, 128.3 (3C), 128.1, 127.9, 127.3, 126.9, 122.0; IR (neat) 3059, 3023, 2923, 2853, 2116, 1491, 1473, 1443, 1280, 1114, 1027, 942, 885 cm$^{-1}$; MS (ESI): m/z=304.11 calc. for C21H15N[M+Na]+, found 304.24.

(E)-1-(2-(4-fluorophenyl)but-1-en-1-yl)-2-isocyanobenzene (9)

$^1$H NMR (500 MHz, CDCl3) δ 7.30 (dd, J=7.9, 1.3 Hz, 1H), 7.10 (t, J=7.5 Hz, 1H), 7.07-7.04 (m, 2H), 7.00 (t, J=7.8 Hz, 1H), 6.94 (m, 2H), 6.76 (d, J=8.0 Hz, 1H), 6.59 (s, 1H), 2.58 (qd, J=7.4, 1.4 Hz, 2H), 1.11 (t, J=7.4 Hz, 3H); $^{13}$C NMR (125 MHz, CDCl3) δ 166.0 162.0 (d, J=244 Hz), 148.0, 136.1 (d, J=4 Hz), 134.6, 130.3, 130.1 (d, J=8 Hz), 128.4, 126.9, 126.6, 125.6, 120.2, 115.4 (d, J=21 Hz), 32.9, 12.8; IR (neat) 2967, 2930, 2117, 1602, 1507, 1222, 1178, 879, 836 cm$^{-1}$; MS (ESI): m/z=274.10 calc. for C17H14FN[M+Na]+, found 274.16.

(E)-1-isocyano-2-(2-(4-(trifluoromethyl)phenyl)but-1-en-1-yl)benzene (10)

$^1$H NMR (500 MHz, CDCl3) δ 7.51 (d, J=8.0 Hz, 2H), 7.31 (dd, J=8.0, 1.3 Hz, 1H), 7.22 (d, J=8.0 Hz, 2H), 7.12 (td, J=7.7, 1.4 Hz, 1H), 7.01 (td, J=7.7, 1.3 Hz, 1H), 6.73 (d, J=8.1 Hz, 1H), 6.67 (s, 1H), 2.61 (qd, J=7.4, 1.5 Hz, 3H), 1.12 (t, J=7.4 Hz, 3H); $^{13}$C NMR (125 MHz, CDCl3) δ 166.1, 147.6, 144.1, 134.1, 130.1, 128.7 (2C), 128.5, 127.2, 126.6, 126.1 (q, J=269 Hz), 125.30, 125.27, 121.1, 32.6, 12.7; IR (neat) 2968, 2931, 2118, 1322, 1164, 1109, 1066, 881, 843 cm$^{-1}$; MS (ESI): m/z=324.10 calc. for C18H14F3N[M+Na]+, found 324.08.

(E)-1-isocyano-2-(2-(3-(trifluoromethyl)phenyl)but-1-en-1-yl)benzene (12)

$^1$H NMR (400 MHz, CDCl3) δ 7.49 (dd, J=8.3, 1.1 Hz, 1H), 7.38-7.26 (m, 4H), 7.12 (td, J=7.7, 1.4 Hz, 1H), 7.00 (td, J=7.7, 1.4 Hz, 1H), 6.67-6.72 (m, 2H), 2.63 (qd, J=7.4, 1.5 Hz, 2H), 1.14 (t, J=7.4 Hz, 3H); $^{13}$C NMR (125 MHz, CDCl3) δ 166.6, 147.7, 141.3, 134.4, 132.2, 131.1, 130.9, 130.4, 129.1, 128.7, 127.5, 126.9, 126.2 (q, J=267 Hz), 125.4, 124.3, 121.4, 32.6, 12.8; IR (neat) 2969, 2118, 1324, 1202, 1163, 1072, 903, 828 cm$^{-1}$; MS (ESI): m/z=324.10 calc. for C18H14F3N[M+Na]+, found 324.08.

(E)-1-isocyano-2-styrylbenzene (13)

$^1$H NMR (400 MHz, CDCl3) δ 7.75 (dd, J=8.4, 1.3 Hz, 1H), 7.64-7.55 (m, 2H), 7.49-7.13 (m, 8H); $^{13}$C NMR (100 MHz, CDCl3) δ 167.0, 136.4, 133.7, 132.7, 129.4, 128.8, 128.6, 128.0, 127.3, 127.0, 125.4, 125.0, 122.2; IR (neat) 3044, 3022, 2119, 1632, 1598, 1480, 1446, 1288, 1263, 1221, 1198, 1092, 959, 875 cm$^{-1}$; MS (ESI): m/z=228.08 calc. for C15H11N[M+Na]+, found 228.00.

(E)-1-isocyano-2-(4-methoxystyryl)benzene (14)

$^1$H NMR (500 MHz, CDCl3) δ 7.71 (dd, J=7.5, 1.2 Hz, 1H), 7.56-7.50 (m, 2H), 7.41-7.36 (m, 2H), 7.27-7.11 (m, 3H), 6.96-6.89 (m, 2H), 3.85 (s, 3H); $^{13}$C NMR (125 MHz, CDCl3) δ 166.7, 160.0, 134.1, 132.2, 129.4, 129.2, 128.4, 127.5, 127.3, 127.0, 125.2, 112.0, 114.3, 55.4; IR (neat) 2924, 2843, 2122, 1633, 1604, 1511, 1481, 1270, 1253, 1172, 1091, 961, 868 cm$^{-1}$; MS (ESI): m/z=258.09 calc. for C16H13NO[M+Na]+, found 258.10.

(E)-1-isocyano-2-(3-methoxystyryl)benzene (15)

$^1$H NMR (500 MHz, CDCl3) δ 7.73 (d, J=7.9 Hz, 1H), 7.42-7.36 (m, 3H), 7.32-7.26 (m, 2H), 7.19 (s, 1H), 7.16 (d, J=7.8 Hz, 1H), 7.10 (m, 1H), 6.88 (dd, J=8.2, 2.4 Hz, 1H), 3.86 (s 3H); $^{13}$C NMR (125 MHz, CDCl3) δ 167.0, 159.9, 137.8, 133.6, 132.6, 129.8, 129.4, 128.0, 127.3, 125.5, 124.9, 122.5, 119.6, 114.2, 112.2, 55.3; IR (neat) 3072, 3034, 2119, 1607, 1581, 1489, 1482, 1448, 1286, 1239, 1157, 1135, 1093, 941, 873 cm$^{-1}$; MS (ESI): m/z=258.09 calc. for C16H13NO[M+Na]+, found 258.00.

(E)-1-isocyano-2-(2-methoxystyryl)benzene (16)

$^1$H NMR (500 MHz, CDCl3) δ 7.80 (d, J=8.0 Hz, 1H); 7.66 (d, J=7.6 Hz, 1H), 7.57 (d, J=16.4 Hz, 1H), 7.46 (d, J=16.5 Hz, 1H), 7.40-7.37 (m, 2H), 7.31 (t, J=8.2 Hz, 1H), 7.24 (d, J=8.0 Hz, 1H), 7.00 (t, J=7.6 Hz, 1H), 6.93 (d, J=8.2 Hz, 1H), 3.91 (s, 3H); $^{13}$C NMR (125 MHz, CDCl3) δ 166.6, 157.2, 134.3, 129.6, 129.2, 127.6, 127.5, 127.1 (2C), 125.4 (2C), 124.8, 122.5, 120.8, 110.9, 55.4; IR (neat) 3033, 2958, 2936, 2834, 2119, 1489, 1463, 1334, 1242, 1191, 1107, 1091, 1031, 992, 965, 879 cm$^{-1}$; MS (ESI): m/z=258.09 calc. for C16H13NO[M+Na]+, found 258.10.

(E)-1-(4-fluorostyryl)-2-isocyanobenzene (17)

$^1$H NMR (500 MHz, Chloroform-d) δ 7.72 (dd, J=8.4, 1.3 Hz, 1H), 7.58-7.52 (m, 2H), 7.40-7.37 (m, 2H), 7.33 (d, J=16.3 Hz, 1H), 7.28 (td, J=7.6, 1.1 Hz, 1H), 7.16 (d, J=16.3 Hz, 1H), 7.10-7.06 (m, 2H); $^{13}$C NMR (125 MHz, CDCl3) δ 167.0, 162.9 (d, J=287 Hz), 133.5, 132.6 (d, J=3 Hz), 131.4, 129.4, 128.61, 128.55, 128.0, 127.3, 125.3, 121.9, 115.8 (d, J=22 Hz); IR (neat) 3045, 2926, 2122, 1567, 1508, 1479, 1265, 1232, 1177, 1159, 960, 933, 817 cm$^{-1}$; MS (ESI): m/z=224.09 calc. for C15H10FN[M+H], found 224.08.

(E)-1-fluoro-2-(2-isocyanostyryl)benzene (18)

$^1$H NMR (500 MHz, CDCl3) δ 7.77 (dd, J=8.0, 1.3 Hz, 1H), 7.70 (td, J=7.7, 1.7 Hz, 1H), 7.48 (d, J=16.5 Hz, 1H), 7.42-7.37 (m, 3H), 7.30-7.27 (m, 2H), 7.18 (td, J=7.6, 1.2 Hz, 1H), 7.10 (m, 1H); $^{13}$C NMR (125 MHz, CDCl3) δ 167.2, 160.5 (d, J=249 Hz), 133.6, 129.9 (d, J=8 Hz), 129.4, 128.3, 127.2, 127.17 (d, J=3 Hz), 125.5, 124.7 (d, J=3 Hz), 125.0, 124.4, 124.3, 124.1 (d, J=3 Hz), 115.8 (d, J=22 Hz); IR (neat) 3057, 2924, 2122, 1635, 1487, 1476, 1452, 1336, 1283, 123, 1212, 1190, 1090, 960, 868 cm$^{-1}$; MS (ESI): m/z=246.07 calc. for C15H10FN[M+Na]+, found 246.00.

(E)-1-(3-fluorostyryl)-2-isocyanobenzene (19)

$^1$H NMR (500 MHz, CDCl3) 57.76 (dd, J=7.8, 1.5 Hz, 1H), 7.42-7.25 (m, 7H), 7.16 (d, J=16.3 Hz, 1H), 7.01-7.04 (m, 1H); $^{13}$C NMR (125 MHz, CDCl3) δ 167.3, 163.2 (d, J=244 Hz), 138.7 (d, J=7.3 Hz), 133.2, 131.5, 130.3 (d, J=8 Hz), 129.5, 128.4, 127.3, 125.6, 125.1, 123.5, 122.8, 115.4 (d, J=21 Hz), 113.5 (d, J=22 Hz); IR (neat) 3072, 3035, 2122, 1608, 1581, 1482, 1448, 1286, 1238, 1183, 1158, 941, 874, 864, 834 cm$^{-1}$; MS (ESI): m/z=246.07 calc. for C15H10FN, found 246.00.

(E)-1-isocyano-2-(4-(trifluoromethyl)styryl)benzene (20)

$^1$H NMR (500 MHz, CDCl3) δ 7.75 (dd, J=7.9, 1.3 Hz, 1H), 7.70-7.61 (m, 4H), 7.50 (d, J=16.3 Hz, 1H), 7.42-7.41 (m, 2H), 7.32 (t, J=6.8 Hz, 1H), 7.22 (d, J=16.3 Hz, 1H); $^{13}$C NMR (125 MHz, CDCl3) δ 167.5, 139.8, 133.0, 131.0, 130.2 (q, J=32 Hz), 129.5, 128.7, 127.4, 127.1, 125.8 (q, J=4 Hz), 125.6, 125.1, 124.7, 124.1 (q, J=270 Hz); IR (neat) 2924, 2123, 1614, 1483, 1321, 1190, 1155, 1104, 1065, 989, 964, 839 cm$^{-1}$; MS (ESI): m/z=296.07 calc. for C16H10FN[M+Na]+, found 295.84.

(E)-1-isocyano-2-(3-(trifluoromethyl)styryl)benzene (21)

$^1$H NMR (500 MHz, CDCl3) δ 7.82-7.77 (m, 3H), 7.61-7.45 (m, 5H), 7.36 (t, J=7.5 Hz, 1H), 7.25 (d, J=16.3 Hz, 1H); $^{13}$C NMR (125 MHz, CDCl3) δ 167.3, 137.2, 133.1, 131.3 (q, J=31 Hz), 131.1, 129.6, 129.5, 129.3, 128.6, 127.4, 125.6, 125.02, 124.99, 124.0, 124.0 (q, J=271 Hz), 123.9; IR (neat) 3049, 2118, 1489, 1341, 1324, 1287, 1224, 1163, 1194, 1114, 1093, 998, 983, 962 cm$^{-1}$; MS (ESI): m/z=296.07 calc. for C16H10FN[M+Na]+, found 296.08.

(E)-1-isocyano-2-(2-(trifluoromethyl)styryl)benzene (22)

$^1$H NMR (500 MHz, CDCl3) δ 7.86 (d, J=7.8 Hz, 1H), 7.76 (d, J=7.9 Hz, 1H), 7.70 (d, J=7.9 Hz, 1H), 7.61-7.54 (m, 2H), 7.45-7.38 (m, 4H), 7.33 (td, J=8.0, 1.3 Hz, 1H); $^{13}$C NMR (125 MHz, CDCl3), δ 167.2, 135.4, 133.2, 132.1, 129.6, 128.7, 128.3, 128.1, 127.9 (q, J=29 Hz), 127.5, 127.3, 126.1, 126.0 (q, J=5.4 Hz), 125.9, 125.3, 124.3 (q, J=269 Hz); IR (neat) 3065, 2926, 2125, 1490, 1311, 1291, 1227, 1202, 1060, 1033, 959 cm$^{-1}$; MS (ESI): m/z=296.07 calc. for C16H10F3N[M+Na]+, found 296.16.

(E)-1-isocyano-2-(4-methylstyryl)benzene (23)

$^1$H NMR (500 MHz, CDCl3) δ 7.75 (dd, J=7.6, 1.1 Hz, 1H), 7.48 (d, J=8.1 Hz, 2H), 7.35-7.41 (m, 3H), 7.26 (td, J=7.4, 1.2 Hz, 1H), 7.20 (d, J=7.1 Hz, 2H), 7.18 (d, J=16.0 Hz, 1H), 2.38 (s, 3H); $^{13}$C NMR (125 MHz, CDCl3) δ 166.8, 138.7, 133.9, 133.6, 132.6, 129.5, 129.4, 127.7, 127.3, 126.9, 125.3, 124.8, 121.1, 21.3; IR (neat) 3023, 2919, 2115, 1630, 1510, 1478, 1445, 1290, 1110, 959, 839 cm$^{-1}$; MS (ESI): m/z=242.09 calc. for C16H13N[M+Na]+, found 242.00.

(E)-1-(4-butylstyryl)-2-isocyanobenzene (24)

$^1$H NMR (500 MHz, CDCl3) δ 7.73 (d, J=8.0 Hz, 1H), 7.50 (d, J=7.9 Hz, 2H), 7.36-7.30 (m, 3H), 7.26 (t, J=7.4 Hz, 1H), 7.22 (d, J=7.5 Hz, 2H), 7.19 (d, J=15.8 Hz, 1H), 2.64 (t, J=7.8 Hz, 2H), 1.63 (m, 2H), 1.39 (m, 2H), 0.95 (t, J=7.4 Hz, 3H); $^{13}$C NMR (125 MHz, CDCl3) δ 166.9, 143.8, 134.0, 133.9, 132.7, 129.4, 128.9, 127.8, 127.3, 127.0, 125.4, 124.8, 121.2, 35.5, 33.6, 22.4, 14.0; IR (neat) 2956, 2928, 2857, 2116, 1736, 1632, 1608, 1480, 1449, 1265, 1241, 1018, 962, 854 cm$^{-1}$; MS (ESI): m/z=284.14 calc. for C19H19N[M+Na]+, found 284.16.

(E)-1-isocyano-2-(4-nitrostyryl)benzene (25)

$^1$H NMR (500 MHz, CDCl3) δ 8.25 (d, J=11.7 Hz, 2H), 7.76 (d, J=10.5 Hz, 1H), 7.70 (d, J=11.7 Hz, 2H), 7.56 (d, J=21.8 Hz, 1H), 7.30-7.46 (m, 3H), 7.24 (d, J=21.8 Hz, 1H); $^{13}$C NMR (125 MHz, CDCl3) δ 167.8, 147.4, 142.7, 132.5, 130.2, 129.6, 129.2, 127.5 (2C), 126.6, 125.8, 124.2, 123.7; IR (neat) 2923, 2842, 2121, 1632, 1510, 1372, 1340, 1299, 1269, 1253, 1226, 1172, 1108, 1091, 1026, 959, 886, 870 cm$^{-1}$; MS (ESI): m/z=273.06 calc. for C15H10N2O2[M+Na]+, found 273.12.

1-(cyclohexylidenemethyl)-2-isocyanobenzene (26)

$^1$H NMR (500 MHz, CDCl3) δ 7.36-7.34 (m, 1H), 7.32 (d, J=7.5 Hz, 1H), 7.26 (d, J=7.5 Hz, 1H), 7.27-7.20 (m, 1H), 2.33 (t, J=6.1 Hz, 2H), 2.25 (t, J=5.6 Hz, 2H), 1.70-1.52 (m, 6H); $^{13}$C NMR (125 MHz, CDCl3) δ 165.2, 147.2, 135.3, 130.3, 128.6, 126.7, 126.6, 125.8, 116.9, 37.3, 29.8, 28.4, 27.7, 26.4; IR (neat) 2927, 2853, 2118, 1479, 1461, 1445, 1343, 1038, 838 cm$^{-1}$; MS (ESI): m/z=220.11 calc. for C14H15N[M+Na]+, found 220.08.

(E)-2-(2-isocyanostyryl)pyridine (27)

$^1$H NMR (500 MHz, CDCl3) δ 8.65-8.63 (m, 1H), 7.88 (d, J=16.2 Hz, 1H), 7.80-7.76 (m, 1H), 7.71 (td, J=7.7, 1.8 Hz, 1H), 7.53 (dt, J=7.9, 1.1 Hz, 1H), 7.45-7.38 (m, 2H), 7.35-7.28 (m, 2H), 7.21 (ddd, J=7.6, 4.8, 1.1 Hz, 1H); $^{13}$C NMR (125 MHz, CDCl3) δ 167.6, 154.9, 149.9, 136.6, 133.1, 132.4, 129.5, 128.7, 127.5, 126.3, 126.1, 125.3, 122.8, 122.0; IR (neat) 3075, 3042, 2118, 1581, 1560, 1485, 1469, 1453, 1427, 1331, 1303, 1279, 1239, 1209, 1180, 1149, 1091, 1049, 992, 9651, 897, 889, 862 cm$^{-1}$; MS (GC-MS) m/z=207.08 calc. for C14H10N2[M+H]+, found 207.1.

(E)-2-(3-isocyanostyryl)pyridine (28)

$^1$H NMR (500 MHz, CDCl3) δ 8.62 (ddd, J=4.8, 1.8, 0.9 Hz, 1H), 7.69 (td, J=7.7, 1.8 Hz, 1H), 7.64-7.55 (m, 3H), 7.43-7.35 (m, 2H), 7.32-7.28 (m, 1H), 7.20 (td, 1H, J=4.8, 1.2 Hz), 7.17 (d, J=16.1 Hz, 1H); $^{13}$C NMR (125 MHz, CDCl3) δ 164.2, 154.7, 149.9, 138.4, 136.7, 130.4, 130.1, 129.8, 128.0, 127.1, 125.8, 124.5, 122.7 (2 C); IR (neat) 3065, 3002, 2925, 2131, 1597, 1583, 1560, 1471, 1441, 1430, 1334, 1302, 1275, 1240, 1209, 1146, 1094, 1083, 978, 951, 892, 863 cm$^{-1}$; MS (GC-MS) m/z=207.08 calc. for C14H10N2[M+H]+, found 207.1.

(E)-2-(4-isocyanostyryl)pyridine (29)

$^1$H NMR (500 MHz, CDCl3) δ 8.62 (ddd, J=4.8, 1.8, 0.9 Hz, 1H), 7.69 (td, J=7.7, 1.8 Hz, 1H), 7.63 (d, J=16.1 Hz, 1H), 7.60-7.57 (m, 2H), 7.40-7.36 (m, 3H), 7.22-7.16 (m, 2H); $^{13}$C NMR (125 MHz, CDCl3) δ 164.8, 154.8, 149.8, 137.9, 136.7, 130.8, 130.1, 127.8 (2 C), 126.8 (2 C), 122.7 (2 C), 122.7; IR (neat) 3056, 2922, 2851, 2130, 1583, 1562, 1505, 1468, 1430, 975 cm$^{-1}$; MS (GC-MS) m/z=207.08 calc. for C14H10N2[M+H]+, found 207.1.

(E)-3-(2-isocyanostyryl)pyridine (30)

$^1$H NMR (500 MHz, CDCl3) δ 8.74 (d, J=2.3, 1H), 8.55 (dd, J=4.8, 1.6 Hz, 1H), 7.95-7.92 (m, 1H), 7.77-7.73 (m, 1H), 7.46 (d, 1H, J=16.3 Hz), 7.44-7.38 (m, 2H), 7.36-7.29 (m, 2H), 7.18 (d, 1H, J=16.3 Hz); $^{13}$C NMR (125 MHz, CDCl3) δ 167.5, 149.5, 149.2, 133.0, 132.9, 132.1, 129.6, 128.9, 128.7, 127.4, 125.6, 125.1, 124.4, 123.7; IR (neat) 3033, 2119, 1583, 1565, 1485, 1450, 1423, 1278, 1228, 1184, 1161, 1091, 1043, 1022, 962, 909 cm$^{-1}$; MS (GC-MS) m/z=207.08 calc. for C14H10N2[M+H]+, found 207.1.

(E)-3-(3-isocyanostyryl)pyridine (31)

$^1$H NMR (500 MHz, CDCl3) δ 8.74 (dd, J=2.3, 0.9 Hz, 1H), 8.53 (dd, J=4.7, 1.6 Hz, 1H), 7.84 (ddd, J=8.0, 2.3, 1.6 Hz, 1H), 7.56-7.52 (m, 2H), 7.44-7.38 (m, 1H), 7.34-7.28 (m, 2H), 7.11 (s, 2H); $^{13}$C NMR (125 MHz, CDCl3) δ 164.4, 149.3, 148.7, 138.3, 132.9, 132.2, 129.9, 128.5, 127.5, 127.4, 127.2, 125.7, 124.2, 123.7; IR (neat) 3027, 2124, 1598, 1581, 1567, 1481, 1435, 1411, 1273, 1182, 1024, 966, 885 cm$^{-1}$; MS (GC-MS) m/z=207.08 calc. for C14H10N2 [M+H]+, found 207.1.

(E)-3-(4-isocyanostyryl)pyridine (32)

$^1$H NMR (500 MHz, CDCl3) δ 8.73 (d, J=2.2 Hz, 1H), 8.53 (dd, J=4.8, 1.6 Hz, 1H), 7.83 (dt, J=8.0, 2.0 Hz, 1H), 7.57-7.51 (m, 2H), 7.41-7.36 (m, 2H), 7.31 (ddd, J=8.0, 4.8, 0.9 Hz, 1H), 7.11 (d, J=4.3 Hz, 2H); $^{13}$C NMR (125 MHz, CDCl3) δ 164.9, 149.2, 148.7, 137.9, 132.9, 132.2, 128.9, 127.4 (2 C), 127.3, 126.9 (2 C), 123.6; IR (neat) 3028, 2920, 2850, 2127, 1644, 1600, 1574, 1567, 1503, 1483, 1421, 1409, 1329, 1304, 1252, 1166, 1130, 1100, 1022.75, 964, 942, 865 cm$^{-1}$; MS (GC-MS) m/z=207.08 calc. for C14H10N2[M+H]+, found 207.1.

(E)-4-(2-isocyanostyryl)pyridine (33)

KKB-1-19: $^1$H NMR (500 MHz, Benzene-d6) δ 8.54-8.46 (m, 2H), 7.40 (d, J=16.3 Hz, 1H), 7.01 (dd, J=8.0, 1.3 Hz, 1H), 6.82-6.71 (m, 4H), 6.60 (td, J=7.7, 1.4 Hz, 1H), 6.49 (d, J=16.3 Hz, 1H); $^{13}$C NMR (125 MHz, CDCl3) δ 167.8, 150.4 (2 C), 143.6, 132.5, 130.1, 129.6, 129.2, 127.5, 126.6, 125.9, 125.3, 121.1 (2 C); IR (neat) 3052, 2922, 2852, 2122, 1592, 1549, 1495, 1479, 1451, 1413, 1309, 1274, 1243, 1213, 1090, 991, 966, 958, 880 cm$^{-1}$; MS (GC-MS) m/z=207.08 calc. for C14H10N2[M+H]+, found 207.1.

(E)-4-(3-isocyanostyryl)pyridine (34)

$^1$H NMR (500 MHz, CDCl3) δ 8.64-8.58 (m, 2H), 7.58-7.52 (m, 2H), 7.42 (t, J=8.1 Hz, 1H), 7.38-7.35 (m, 2H), 7.34-7.31 (m, 1H) 7.23 (d, J=16.3 Hz, 1H), 7.05 (d, J=16.3 Hz, 1H); $^{13}$C NMR (125 MHz, CDCl3) δ 164.7, 150.4 (2 C), 143.7, 137.8, 130.8, 129.9, 128.4, 127.8, 127.3, 126.2, 124.5, 121.0 (2 C); IR (neat) 3056, 3029, 2922, 2128, 1591, 1549, 1494, 1478, 1450, 1415, 1242, 1217, 1174, 991, 971, 922, 893, 874, 859 cm$^{-1}$; MS (GC-MS) m/z=207.08 calc. for C14H10N2[M+H]+, found 207.1.

(E)-4-(4-isocyanostyryl)pyridine (35)

$^1$H NMR (500 MHz, CDCl3) δ 8.64-8.59 (m, 2H), 7.60-7.53 (m, 2H), 7.42-7.35 (m, 4H), 7.26 (d, 1H, J=16.3 Hz), 7.04 (d, J=16.3 Hz, 1H); $^{13}$C NMR (125 MHz, CDCl3) δ 165.3, 150.4 (2 C), 143.8, 137.3, 131.1, 128.4, 127.8 (2 C), 126.9 (2 C), 126.2, 121.0 (2 C); IR (neat) 3031, 2923, 2118, 1582, 1559, 1504, 1486, 1469, 1453, 1427, 1331, 1302, 1279, 1239, 1209, 1180, 1148, 1091, 992, 962, 942, 898, 858 cm$^{-1}$; MS (GC-MS) m/z=207.08 calc. for C14H10N2[M+H]+, found 207.1.

(E)-1-isocyano-3-styrylbenzene (36)

$^1$H NMR (500 MHz, CDCl3) δ 7.54-7.50 (m, 4H), 7.41-7.35 (m, 3H), 7.34-7.28 (m, 1H), 7.26-7.23 (m, 1H), 7.14 (d, J=16.3 Hz, 1H), 7.04 (d, J=16.3 Hz, 1H); $^{13}$C NMR (125 MHz, CDCl3) δ 164.1, 139.0, 136.4, 131.1, 129.7, 128.8 (2 C), 128.4, 127.4, 127.1, 126.8 (2 C), 126.4, 125.1, 124.0; IR (neat) 3024, 2922, 2126, 1597, 1578, 1496, 1485, 1472, 1449, 1267, 1226, 1168, 1145, 1081, 1074, 965, 911, 884 cm$^{-1}$; MS (GC-MS) m/z=206.09 calc. for C15H11N[M+H]+, found 206.1.

(E)-1-isocyano-4-styrylbenzene (37)

$^1$H NMR (500 MHz, CDCl3) δ 7.54-7.49 (m, 4H), 7.41-7.35 (m, 4H), 7.33-7.28 (m, 1H), 7.16 (d, J=16.3 Hz, 1H), 7.08 (d, J=16.3 Hz, 1H); $^{13}$C NMR (125 MHz, CDCl3) δ 164.5, 138.6, 136.5, 131.1 (2 C), 128.8 (2 C), 128.4 (2 C), 127.2 (2 C), 126.8 (3 C), 125.2; IR (neat) 3023, 2920, 2850, 2123, 1633, 1576, 1503, 1448, 1417, 1335, 1305, 1220, 1198, 1160, 1107, 1073, 967, 950, 918, 866 cm$^{-1}$; MS (GC-MS) m/z=206.09 calc. for C15H11N[M+H]+, found 206.1.

2-isocyano-5-methyl-4'-(trifluoromethyl)-1,1'-biphenyl (50)

Prepared according to a procedure reported by Studer (Zhang, B. et al, *Angew. Chem., Int. Ed.* 2013, 52, 10792) from 2-bromo-4-methylanaline and 4-(trifluoromethyl)phenylboronic acid. $^1$H NMR (500 MHz, CDCl3) δ 7.77 (d, J=8.1 Hz, 2H), 7.66 (d, J=8.1 Hz, 2H), 7.44 (d, J=8.6 Hz, 1H), 7.26-7.27 (m, 2H), 2.47 (s, 3H); 13C NMR (125 MHz, CDCl3) 166.8, 140.9, 140.4, 137.3, 131.1, 130.4 (q, J=32 Hz), 129.8, 129.6, 127.9, 125.7, 124.2 (q, J=270 Hz), 122.3, 21.3; IR (cm$^{-1}$1): 2922, 2125, 1620, 1571, 1493, 1396, 1328, 1198, 1179, 1155, 1110, 965, 952, 897, 880, 845; MS (ESI): m/z=262.09 calc. for C15H10F3N[M+H]+, found 262.2.

1-isocyano-2-phenethylbenzene (53)

$^1$H NMR (500 MHz, CDCl3) δ 7.37 (dd, J=7.8, 1.4 Hz, 1H), 7.33-7.28 (m, 3H), 7.27-7.19 (m, 5H), 3.07 (dd, J=8.9, 7.6 Hz, 2H), 2.95 (dd, J=8.9, 5.6 Hz, 2H); $^{13}$C NMR (125 MHz, CDCl3) δ 166.1, 140.8, 138.2, 130.0, 129.4, 128.6 (2 C), 128.5 (2 C), 127.1, 126.9, 126.2, 126.1, 36.0, 34.7; IR (neat) 3063, 3028, 2926, 2855, 2119, 1603, 1496, 1487, 1453 cm⁻¹; MS (GC-MS) m/z=208.11 calc. for C15H13N [M+H]+, found 208.1.

Compounds 46, 49 and 51 were prepared according to the literature procedure (Zhang, B. et al., *Angew. Chem., Int. Ed.* 2013, 52, 10792) and their spectral data match with the reported ones. Compounds 5, 6, 11 (Zhang, B. & Studer, A., *Org. Lett.* 2014, 16, 1216), 42 (Tanaka, R. et al., *J. Am. Chem. Soc.* 2008, 130, 2904), and 43 (Hahn, B. T. et al., *Angew. Chem., Int. Ed.* 2010, 49, 1143) were prepared according to the representative procedure aforementioned and their spectral data match with the reported ones.

Biological Materials and Evaluation Methods:

Bacterial Strains and Reagents.

Clinical isolates of MRSA, vancomycin-intermediate *S. aureus* (VISA), and vancomycin-resistant *S. aureus* (VRSA) were obtained through the Network of Antimicrobial Resistance in *Staphylococcus aureus* (NARSA) program (FIG. 6). Vancomycin hydrochloride (Gold Biotechnology, St. Louis, Mo., USA) and linezolid (Chem-Impex International, Inc., Wood Dale, Ill., USA) powders were purchased commercially and dissolved in DMSO to prepare a stock 10 mM solution.

Assessment of Antimicrobial Activity of the Isonitrile Compounds Against Multidrug-Resistant *S. aureus* Strains.

The minimum inhibitory concentration (MIC) of each compound and linezolid was determined against eight different strains of MRSA, VISA, and VRSA using a modified version of the broth microdilution method, outlined by the CLSI. Institute CaLS, *Methods for Dilution Antimicrobial Susceptibility Tests for Bacteria That Grow Aerobically—Seventh Edition: Approved Standard M7-A7*. 7 ed. Wayne, Pa. 2011. The same analysis was performed with vancomycin against the VISA and VRSA strains tested. A bacterial suspension (~1 Å~105 CFU/mL) was prepared in Tryptic soy broth (TSB) and then transferred to a microtiter plate. Each agent tested was added (in triplicate) to wells in the first row of the plate and then serially diluted downward. Plates were incubated at 37° C. for 18-20 h before the MIC was determined as the lowest concentration of each test agent where bacterial growth was not visible.

Toxicity Analysis of Selected Isonitrile Compounds Tested Against Mammalian Cells.

Selected isonitrile compounds were assayed at concentrations of 16 µM, 32 µM, 64 µM, and 128 µM against a murine macrophage (J774) cell line to assess if the compounds exhibited toxicity to mammalian cells in vitro. Cells were cultured in Dulbeco's modified Eagle's medium (Sigma-Aldrich, St. Louis, Mo., USA) with 10% fetal bovine serum (USA Scientific, Inc.) at 37° C. with 5% CO2. Controls received DMSO alone at a concentration equal to that in drug-treated cell samples. The cells were incubated with each compound (in triplicate) in a 96-well tissue-culture plate at 37° C. and 5% CO2 for 2 h prior to addition of the assay reagent MTS 3-(4,5-dimethylthiazol-2-yl)-5-(3-carboxymethoxyphenyl)-2-(4-sulfophenyl)-2H-tetrazolium) (Promega, Madison, Wis., USA). Absorbance readings (at OD490) were taken using a kinetic microplate reader (Molecular Devices, Sunnyvale, Calif., USA). The quantity of viable cells after treatment with each compound was expressed as a percentage of the viability of DMSO-treated control cells (average of triplicate wells±standard deviation). Statistical analysis was performed (comparing cells treated with compound versus cells treated with DMSO) using the paired t-test (P<0.05) utilizing Microsoft EXCEL software.

Caco-2 Permeability Analysis of Compound 13.

The ability of compound 13, ranitidine (low permeability control), warfarin (high permeability control), and talinolol (P-glycoprotein efflux substrate), to effectively permeate across a biological membrane was assessed using a Caco-2 cell monolayer, as described elsewhere. Mohammad, H. et al., *J. Antibiot.* 2014, doi:10.1038/ja.2014, 142. The amount of permeation was determined both from the apical (A) to basolateral (B) direction and the basolateral (B) to apical (A) direction. Data for apparent permeability (Papp) and the efflux ratio (RE) were determined as explained elsewhere. Mohammad, H. et al., ibid. An RE>2 indicates the test agent may be a potential substrate for P-glycoprotein or other active efflux transporters.

Kinetic Solubility Screen.

A kinetic solubility analysis of compound 13, reserpine, tamoxifen, and verapamil was performed as has been described elsewhere. Mohammad, H. et al., ibid. The solubility limit (in µM) reported is the maximum concentration of each test agent where turbidity was not observed. Values below 1 µM indicate compound is insoluble, values between 1 to 100 µM indicate partial aqueous solubility, and values above 100 µM indicate test agent is fully soluble.

Metabolic Stability Analysis Using Pooled Human Liver Microsomes.

To analyze the stability of compound 13 to metabolic processes in the liver, this compound was incubated in duplicate with pooled human liver microsomes at 37° C. (for 60 min), using a similar protocol described elsewhere, with two modifications. Zhang, W. et al., *Bioorgan. Med. Chem.* 2012, 20, 1029; Papadopoulou, M. V. et al., *Future Med. Chem.* 2013, 5, 1763. First, the reaction mixture utilized 0.3 mg/mL microsomal protein. Additionally, samples were collected after 0 and 60 min and analyzed accordingly. Data are reported as % remaining by dividing by the time zero concentration value.

It should be understood, of course, that the foregoing relates to exemplary embodiments of the invention and that modifications may be made without departing from the spirit and scope of the invention as set forth in the following claims.

We claim:

1. A method for inhibiting MRSA comprising contacting MRSA with an isonitrile compound having the structure:

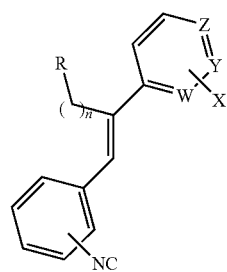

wherein R is a hydrogen, an alkyl, a cycloalkyl, a heteroalkyl, or an aryl group;
n is an integer from 0 to 4;
X is hydrogen, a C1 to C3 alkyl group, a halogen, alkyloxy, trihalomethyl, or a nitro group;
W, Y, and Z are each independently —CH— or N with one and only one of W, Y, or Z is N; and
pharmaceutically acceptable salts thereof.

2. The method of claim 1, wherein R is hydrogen and n is 0.

3. The method of claim 1, wherein the amount the isonitrile compound is from about 50 μM to about 100 μM.

4. The method of claim 1, wherein the strain of MRSA is NRS1, NRS72, NRS119, NRS382, NRS383, NRS384, NRS385, NRS386, VRS2, or combinations thereof.

5. A method for treating a patient having a MRSA infection comprising administering to the patient a therapeutically effective amount of an isonitrile compound having the structure:

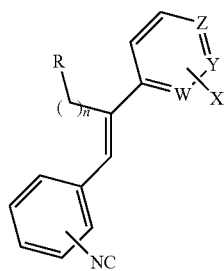

wherein R is a hydrogen, an alkyl, a cycloalkyl, a heteroalkyl, or an aryl group;

n is an integer from 0 to 4;

X is hydrogen, a C1 to C3 alkyl group, a halogen, alkyloxy, trihalomethyl, or a nitro group;

W, Y, and Z are each independently —CH— or N with one and only one of W, Y, or Z is N; and pharmaceutically acceptable salts thereof.

6. The method of claim 5, wherein R is hydrogen and n is 0.

7. The method of claim 5, wherein the strain of MRSA is NRS1, NRS72, NRS119, NRS382, NRS383, NRS384, NRS385, NRS386, VRS2 or combinations thereof.

8. The method of claim 6, wherein the isonitrile compound is administered with a second antibacterial compound.

* * * * *